United States Patent
Lagally et al.

(10) Patent No.: US 11,864,465 B2
(45) Date of Patent: Jan. 2, 2024

(54) INTEGRATION OF SEMICONDUCTOR MEMBRANES WITH PIEZOELECTRIC SUBSTRATES

(71) Applicants: Wisconsin Alumni Research Foundation, Madison, WI (US); University of Hamburg, Hamburg (DE)

(72) Inventors: Max G. Lagally, Madison, WI (US); Abhishek Bhat, Fremont, CA (US); Frank Steele Flack, Madison, WI (US); Shelley Ann Scott, Madison, WI (US); Robert H. Blick, Hamburg (DE)

(73) Assignee: Wisconsin Alumni Research Foundation, Madison, WI (US)

(*) Notice: Subject to any disclaimer, the term of this patent is extended or adjusted under 35 U.S.C. 154(b) by 440 days.

(21) Appl. No.: 16/881,305

(22) Filed: May 22, 2020

(65) Prior Publication Data
US 2021/0367138 A1    Nov. 25, 2021

(51) Int. Cl.
*H01L 41/312* (2013.01)
*H10N 30/072* (2023.01)
*H10N 30/20* (2023.01)
*H10N 30/80* (2023.01)
*H10N 30/87* (2023.01)
*H10N 30/853* (2023.01)

(52) U.S. Cl.
CPC ......... *H10N 30/072* (2023.02); *H10N 30/206* (2023.02); *H10N 30/802* (2023.02); *H10N 30/8554* (2023.02); *H10N 30/875* (2023.02)

(58) Field of Classification Search
CPC . H01L 41/312; H01L 41/042; H01L 41/0475; H01L 41/0986; H01L 41/1876; H01L 41/25; H01L 41/09; G01N 33/48721; B06B 1/0644
See application file for complete search history.

(56) References Cited

U.S. PATENT DOCUMENTS

| | | | |
|---|---|---|---|
| 10,176,991 B1 | 1/2019 | Lagally et al. | |
| 2007/0257580 A1* | 11/2007 | Chen | B81C 1/0038 310/328 |
| 2008/0020573 A1* | 1/2008 | Birkmeyer | B41J 2/1628 438/689 |

(Continued)

FOREIGN PATENT DOCUMENTS

| | | | | |
|---|---|---|---|---|
| CN | 101510482 A | * | 8/2009 | |
| EP | 3591724 A1 | * | 1/2020 | H01L 41/0477 |

(Continued)

OTHER PUBLICATIONS

Namba et al., "Direct bonding of piezoelectric crystal onto silicon," Appl. Phys. Lett. 67, 3275 (1995).

(Continued)

*Primary Examiner* — Jarrett J Stark
(74) *Attorney, Agent, or Firm* — Bell & Manning, LLC

(57) ABSTRACT

Piezoelectrically actuated devices constructed from thin semiconductor membranes bonded directly to piezoelectric substrates are provided. Methods for fabricating these devices are also provided. The bonding of the semiconductor to the piezoelectric material does not require the use of any intermediate layers, such as bonding agents.

13 Claims, 2 Drawing Sheets

(56) References Cited

U.S. PATENT DOCUMENTS

| | | | |
|---|---|---|---|
| 2011/0132098 A1* | 6/2011 | Ballandras | G01L 11/06 |
| | | | 29/25.35 |
| 2011/0281407 A1 | 11/2011 | Forbes et al. | |
| 2014/0055008 A1 | 2/2014 | Ito | |
| 2015/0215706 A1* | 7/2015 | Sparks | G01L 9/008 |
| | | | 73/717 |
| 2016/0025655 A1 | 1/2016 | Blick et al. | |
| 2017/0025596 A1* | 1/2017 | Qiu | H03H 9/0014 |
| 2018/0153512 A1 | 6/2018 | Akkaraju et al. | |
| 2019/0285196 A1* | 9/2019 | Giusti | B81C 1/00182 |
| 2019/0322524 A1 | 10/2019 | Lee et al. | |
| 2020/0013947 A1* | 1/2020 | Le Rhun | H01L 41/319 |
| 2020/0092666 A1 | 3/2020 | Lagally et al. | |
| 2020/0313640 A1 | 10/2020 | Hori et al. | |
| 2021/0034935 A1* | 2/2021 | Ballandras | H03H 3/08 |
| 2021/0367138 A1* | 11/2021 | Lagally | H01L 41/25 |

FOREIGN PATENT DOCUMENTS

| | | | | |
|---|---|---|---|---|
| FR | 3012700 A1 * | 5/2015 | | H01L 41/00 |
| FR | 3083004 A1 * | 12/2019 | | H01L 41/0477 |
| KR | 10-2020-0033326 | 3/2020 | | |
| WO | WO-2012035491 A1 * | 3/2012 | | G01P 5/02 |
| WO | WO2016/007250 | 1/2016 | | |

OTHER PUBLICATIONS

Eda et al., "Novel Composite Piezolectric Materials Using Direct Bonding Techniques," 1995 IEEE Ultrasonics Symposium, pp. 921-924.

Aktakka, Ethem Erkan, Rebecca L. Peterson, and Khalil Najafi. "Wafer-level integration of high-quality bulk piezoelectric ceramics on silicon." *IEEE transactions on electron devices* 60.6 (2013): 2022-2030.

Tanaka, Katsuhiko, et al. "Wafer bonding of lead zirconate titanate to Si using an intermediate gold layer for microdevice application." *Journal of Micromechanics and Microengineering* 16.4 (2006): 815.

Wang, Zhihong, Jianmin Miao, and Chee Wee Tan. "Acoustic transducers with a perforated damping backplate based on PZT/ silicon wafer bonding technique." *Sensors and Actuators A: Physical* 149.2 (2009): 277-283.

Wu et al., "Silicon-Based Micromachining Process for Flexible Electronics," published Apr. 3, 2019; DOI: 10.5772/intechopen. 83347.

Wu et al., "Parametric excitation of a SiN membrane via piezoelectricity," AIP Advances 8, 015209 (2018).

Naserbakht et al., "Stress-Controlled Frequency Tuning and Parametric Amplification of the Vibrations of Coupled Nanomembranes," Appl. Sci. Sep. 2019, 4845.

Ziss et al., "Comparison of different bonding techniques for efficient strain transfer using piezoelectric actuators," *J Appl Phys.*; 121, available in PMC May 16, 2017.

Koh, Keishin, et al. "Bonding technology of semiconductor film on piezoelectric substrate using epitaxial lift-off technology." *Japanese Journal of Applied Physics* 40.5S (2001): 3734.

Kim et al.,"Micro-LEGO for MEMS," *Micromachines* Oct. 2019, 267.

Wang et al "The evolution of nanopore sequencing," www.frontiersin. org, Jan. 2015, vol. 5, Article 449, 20 pages.

International Search Report and Written Opinion for PCT/US2021/ 029343, dated Oct. 22, 2021.

Hui, Yeung Yu, et al. "Exceptional tunability of band energy in a compressively strained trilayer MoS2 sheet." *ACS nano* 7.8 (2013): 7126-7131.

Zhou, Ling, et al. "Chemomechanical polishing of silicon carbide." *Journal of the Electrochemical Society* 144.6 (1997): L161.

Shivaraman, Shriram, et al. "Free-standing epitaxial graphene." *Nano letters* 9.9 (2009): 3100-3105.

Zhou, Jian, et al. "Surface acoustic wave devices with graphene interdigitated transducers." *Journal of Micromechanics and Microengineering* 29.1 (2018): 015006.

European Patent Office. Extended European Search Report. Reference 24306P/EP, Application No./Patent No. 21809801.0-1212 / 4154328 PCT/US2021029343. dated Oct. 13, 2023, pp. 1-9.

Heifi Kejing Material Technology Co. PMN-PT crystal. Website—original in Chinese. Available on or before Nov. 19, 2019. https:// web.archive.org/web/20191119235046/http:/www.kjmti.com/product/ 15466.html.

Heifi Kejing Material Technology Co. PMN-PT crystal. Website—English Translation. Available on or before Nov. 19, 2019. https:// web.archive.org/web/20191119235046/http:/www.kjmti.com/product/ 15466.html.

* cited by examiner

INTEGRATION OF SEMICONDUCTOR MEMBRANES WITH PIEZOELECTRIC SUBSTRATES

REFERENCE TO GOVERNMENT RIGHTS

This invention was made with government support under DE-FG02-03ER46028 awarded by the US Department of Energy. The government has certain rights in the invention.

BACKGROUND

Piezoelectric materials have been used in transducers to reversibly transfer strain to thin films of other materials, including semiconductors, for the purpose of tuning the electrical, optical, and electrooptical properties of those materials. In such transducers, the magnitude of strain induced in the thin film is proportional to the electric field applied across the piezoelectric material. Devices that have been fabricated based on this design include those in which piezoelectric actuation is used to tune the optical emission spectra and the electroacoustic properties of semiconductor films. However, conventional piezoelectric transducers require a bonding agent between the piezoelectric substrate and the semiconductor in order to bond the two materials together. These bonding agents have included polymer adhesives (e.g., parylene gluing), metal layers (e.g., eutectic bonding), and glass.

Unfortunately, intermediate bonding layers between a semiconductor film and a piezoelectric substrate can affect strain transfer between the piezoelectric substrate and the semiconductor film and attenuate the acoustic amplitude of a piezoelectric transducer. Moreover, bonding agents may be incompatible with biological environments, limiting the applications in which piezoelectric transducers with bonding layers can be used.

SUMMARY

Piezoelectric transducers composed of semiconductor-piezoelectric composite structures and methods for fabricating the transducers are also provided.

One embodiment of a piezoelectric transducer includes: a piezoelectric substrate having a membrane-bonding surface with a surface roughness of no greater than 100 nm RMS; a semiconductor membrane having a thickness of 5 μm or less bonded directly to the membrane-bonding surface; and a set of electrodes in electrical communication with the piezoelectric substrate and configured to apply an electric signal to the piezoelectric substrate.

One embodiment of a method of forming a piezoelectric transducer includes the steps of: forming a semiconductor membrane having a thickness of no greater than 5 μm; polishing a membrane-bonding surface of a piezoelectric substrate to a surface roughness of no greater than 100 nm RMS; and directly bonding the semiconductor membrane to the membrane-bonding surface of the piezoelectric substrate.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
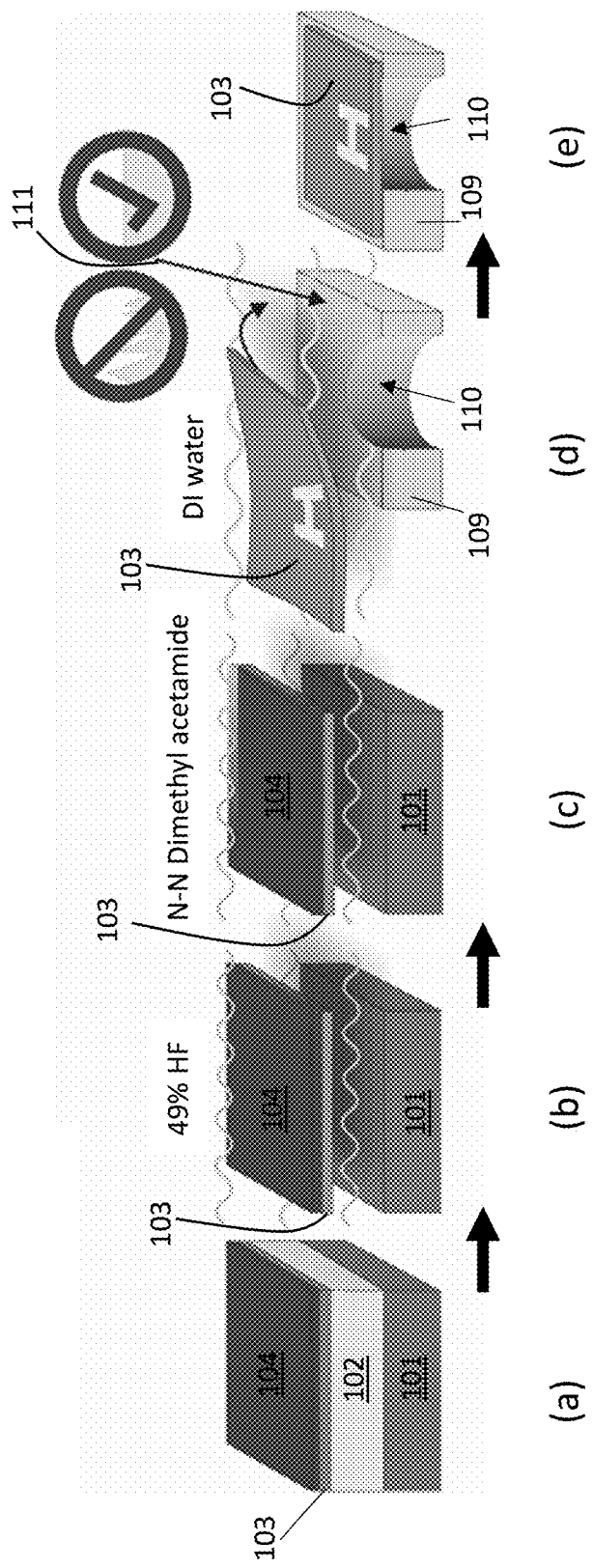
FIG. 1. Schematic diagram of one embodiment of a method for the bonding of a free-standing semiconductor membrane with a piezoelectric ceramic substrate.

Semiconductor-piezoelectric composite structures constructed from thin semiconductor membranes bonded to piezoelectric substrates are provided. Methods for fabricating the structures are also provided. The semiconductor membranes can be actuated piezoelectrically by applying an electric signal to the substrate. This actuation of the semiconductor membrane can be used to provide a transducer that modulates various properties of the semiconductor membranes, making them useful in a variety of devices. Examples of devices into which the composite semiconductor-piezoelectric devices can be incorporated include chemical, including biochemical, sensors, optoelectronics, and strain-responsive electronics.

Aspects of the various inventions described herein are based, at least in part, on the inventors' discovery that the use of a piezoelectric substrate having an ultra-smooth surface enables the bonding of a semiconductor membrane directly to the surface of a piezoelectric substrate without the use of any bonding agents. The directly bonded membrane adheres strongly to the piezoelectric substrate and the bonding can provide a flat (i.e., unwrinkled) membrane that well suited for microelectronic device integration.

The semiconductor membrane can be formed and microelectronic devices can be patterned on the semiconductor membrane prior to bonding the semiconductor membrane to the piezoelectric substrate. This offers the benefit of combining two pre-fabricated and well-defined device materials and eliminates the need to modify the semiconductor membrane and/or the piezoelectric substrate after the two layers have been integrated.

The semiconductor membranes are thin films of a semiconductor material. The use of a thin semiconductor membrane allows for the piezoelectric actuation of membrane properties, including optoelectronic (e.g., photoluminescence and electroluminescence) and/or electroacoustical properties. The semiconductor membranes have thicknesses of 5 μm or less, including thicknesses of 2 μm or less and thicknesses of 1 μm or less. Some embodiments of the semiconductor membranes have thicknesses of less than 1 μm (1000 nm). This includes semiconductor membranes having a thickness of 500 nm or less, semiconductor membranes having a thickness of 200 nm or less, semiconductor membranes having a thickness of 100 nm or less, and semiconductor membranes having a thickness of 50 nm or less. By way of illustration, some of the semiconductor membranes have thicknesses in the range from 5 nm to 500 nm. The semiconductor membranes can be single-crystalline, polycrystalline, or amorphous. The use of single-crystalline semiconductor membranes is advantageous because the membranes can have standard microelectronic devices patterned on the semiconductor element prior to bonding to a piezoelectric substrate, and because the membranes are very conformal, which allows them to bond better than their bulk counterparts.

The semiconductor membranes can be obtained by releasing a thin film of semiconductor material from a support substrate or a substrate structure on which the semiconductor film was originally grown. For example, a silicon membrane can be obtained by releasing the silicon device layer from a silicon-on-insulator substrate, as illustrated in panels (a)-(c) of FIG. 1. The process begins with silicon-on-insulator (SOI) wafer that includes a handle substrate 101, a buried oxide (BOX) layer 102, and a thin single-crystalline silicon device layer 103. In the embodiment of the process shown in FIG. 1, panels (a) through (c), a layer of photoresist (PR) 104 is applied to the top surface of silicon device layer 103 using, for example, spin-coating. Silicon device layer 103 is then released from handle substrate 101 by submerging silicon device layer 103 in a solution comprising an etchant that is selective for silicon oxide, such as hydrofluoric acid (HF), to selectively etch away BOX layer 102 (FIG. 1, panel (b)). Optionally, silicon device layer 103 can be thinned using, for example, a chemical or mechanical polish prior to the application of photoresist 104 and/or release from sacrificial oxide layer 102.

Photoresist layer 104 serves as a buoyancy aid and protective layer during membrane release (FIG. 1, panel (b)). Thus, the photoresist is desirably selected such that it renders the released semiconductor/photoresist bilayer buoyant in the etchant solution. The use of a buoyancy aid may be advantageous for very thin semiconductor membranes (e.g., membranes having thicknesses of about 50 nm or less) because it helps to prevent the released membranes from settling back onto handle substrate 101 after release. However, the use of photoresist layer 104 is not necessary, particularly for thicker membranes. If photoresist layer 104 is used, it can be removed from semiconductor membrane 103 after release using a suitable PR stripper (FIG. 1, panel (c)). Other suitable resists include electron-beam (E-beam) resists, such as novolak-based resists, including S1813 available from Dow (Shipley), and acrylate-styrene co-polymer resists, such as ZEP520, a copolymer of α-chloromethacrylate and α-methylstyrene, available from Zeon Chemicals.

Semiconductors other than silicon can be used as the semiconductor membrane. These include other Group IV semiconductors and semiconductor alloys, such as germanium (Ge) and silicon-germanium alloys (SiGe), and alloys of germanium and/or silicon and tin, such as GeSn and SiGeSn alloys. Other suitable semiconductors include Group III-V semiconductors; Group II-VI semiconductors; and metal dichalcogenide semiconductors. The Group III-V and Group II-VI semiconductors include binary, ternary, and higher compound semiconductors. Examples of Group III-V semiconductors include GaAs, AlGaAs, InGaAs, AlAs, InAlAs, InP, GaInP, GaP, GaN, InGaN, InAlN, and AlGaN. Examples of Group II-VI semiconductors include oxides, such as ZnO. Metal dichalcogenide semiconductors include $WS_2$. Thin films of these other semiconductors can be released from their growth substrates by selectively etching away the substrate or an intervening sacrificial layer, such as a buried oxide, in a manner analogous to that described above for silicon.

Microelectronic devices can be formed on the semiconductor membrane before or after it is released from its substrate and prior to or after bonding the membrane to the piezoelectric substrate. The microelectronic devices can be formed using, for example, lithography, etching, or printing. Microelectronic devices will generally include active and passive electrical components that make up a circuit, including electrical contacts, transmission lines, capacitors, transistors, and the like. The specific components and their location on the membrane will depend on the particular application for which the devices are designed.

In some embodiments of the semiconductor membrane-piezoelectric substrate structures, the piezoelectric substrate defines an aperture and the semiconductor membrane is bonded to the piezoelectric substrate around the perimeter of the aperture, such that a portion of the semiconductor membrane is suspended over the aperture. In embodiments of the structures that include an aperture in the piezoelectric substrate, the components of the microelectronic devices may be positioned such that they are located over the portion of the semiconductor membrane that is suspended over the aperture in the piezoelectric substrate, and/or they may be positioned such that they are located over the piezoelectric material substrate around the aperture.

Once semiconductor membrane 103 is released, it can be transferred onto a piezoelectric substrate 109 and then bonded to the surface of that substrate, as illustrated in panels (d) and (e) of FIG. 1. The transfer can be a wet transfer, whereby semiconductor membrane 103 is lifted out of solution by piezoelectric substrate 109, or a dry transfer, whereby semiconductor membrane 103 is removed from the etching solution and then transferred onto piezoelectric substrate 109 using a stamp. In the particular embodiment shown here, the piezoelectric substrate defines an aperture 110 through its thickness. However, for many device applications, no aperture is needed. The "H" on panels (d) and (e) represents electronic components integrated on the suspended portion of semiconductor membrane 103.

The piezoelectric substrate can be a bulk material, such as a wafer. Piezoelectric materials that can be used include lead zirconium titanate (PZT), which may be undoped or doped with La, Mn, or Nb, lithium niobate, lead magnesium niobate-lead titanate (PMN-PT), lead zinc niobate-lead titanate (PZN-PT), $K_xNa_{1-x}NbO_3$ (KNN), $Ba_xSr_{1-x}TiO_3$ (BST), $Ba(Ti_xZr_{1-x})O_3$—$(Ba_yCa_{-y})TiO_3$ (BCTZ), or $Na_xBi_yTiO_3$—$BaTiO_3$ (NBT-BT), $LiNbO_3$, gallium phosphate, quartz, and tourmaline.

In order to facilitate direct bonding between the semiconductor membrane and the surface of the piezoelectric substrate, the surface of the piezoelectric substrate should have a low surface roughness. Therefore, prior to transferring the semiconductor membrane to the piezoelectric substrate, the membrane-bonding surface 111 of piezoelectric substrate 109 can be polished to reduce its RMS roughness in order to enable high-quality, direct bonding between the membrane and the substrate. The piezoelectric substrates can be polished using mechanical polishing with readily available polishing media suitable for ceramics. Generally, the surface should be polished to an RMS roughness of 100 nm or less, including 75 nm or less, and 50 nm or less. RMS surface roughness, as measured by atomic force microscopy.

As used herein, the phrases "direct bonding" or "bonded directly to" mean that the surface of semiconductor membrane and the surface of the piezoelectric substrate are in direct physical contact with one another at an interface and that no other material is applied or inserted between them at that interface in order to create a bond between the semiconductor membrane and the piezoelectric substrate. Thus, the methods described herein are distinguishable from methods in which a semiconductor is bonded to a substrate using bonding agents, where the term "bonding agent" refers to a material, such as a chemical adhesive or a deliberate chemical surface functionalization, that is disposed between the semiconductor membrane and the piezoelectric substrate that strengthens the bonding of the semiconductor membrane to the piezoelectric substrate. Such bonding agents include polymer-based adhesives, such as parylene and epoxy resins, and intervening layers of glass or metals, including metal thermo compression layers and/or metal eutectics, such as gold eutectics or gold-tin eutectics. It should be noted, however, that electrical components, such as electrodes and/or electrical interconnects can be located between the semiconductor membrane and the piezoelectric substrate, provided that there still exists direct bonding of the semiconductor membrane to a bonding surface of the piezoelectric membrane around such electrical components. And, while in some embodiments of the structures, one or more electrical components are located between the semiconductor membrane and the piezoelectric substrate, in other embodiments there are no electrical components disposed between the membrane and the substrate.

The bonding of the transferred semiconductor membrane to the membrane-bonding surface of the piezoelectric substrate can be carried out by annealing in an ambient environment. Annealing is not, however, necessary. The membrane may simply be allowed to dry without annealing. If annealing is used, illustrative annealing conditions include temperatures up to 120° C. (e.g., 100° C. to 130° C.) for up to 30 min (e.g., 5 min to 30 min) to eliminate water. As a result of the bonding process, semiconductor membrane 104 covers aperture 110 and is directly bonded to surface 111 around the perimeter of aperture 110. In the embodiment shown in FIG. 1, aperture 110 is a round hole (shown bisected in the cross-sectional view of FIG. 1). However, the perimeter of the aperture need not be round; it can have a variety of regular or irregular shapes, including oval, square, rectangular, and the like, and the aperture need not extend through the entire thickness of the piezoelectric substrate. Moreover, as previously noted, the aperture need not be present.

The semiconductor-piezoelectric composite structures made according to the methods described herein use the piezoelectric effect to convert electrical energy into a mechanical displacement. This enables a number of piezoelectrically actuated devices, including chemical sensors, optoelectronics, strain-responsive electronics, and electroacoustic devices.

A set of two or more electrodes can be used to apply an electric signal to the piezoelectric substrate to elicit a piezoelectric response. For example, an external stress can be applied to the semiconductor membrane by applying a voltage V between a first electrode and a second electrode, both of which are in electrical communication with the piezoelectric substrate. In some embodiments of the structures, one or more of the electrodes forms and antenna. The electrodes can be placed, for example, on opposing sides or surfaces of the piezoelectric substrate or on the same surface of the piezoelectric substrate. The electrodes can be in direct contact with the piezoelectric substrate or can make contact with the piezoelectric substrate through one or more electrically conducting layers. The application of a voltage across the piezoelectric substrate using an external electric signal source in electrical communication with the electrodes creates a distortion of the piezoelectric material that actuates strain in the semiconductor membrane. This strain actuation can be harnessed for a variety of device applications. For example, a DC signal applied to the piezoelectric substrate can be used to induce an expansion and contraction of the piezoelectric substrate, thereby imparting strain to the adherent semiconductor membrane.

The controlled and reversible application of strain to the semiconductor membrane is useful in controlling the efficiency and/or wavelength of light emission from photoluminescent or electroluminescent semiconductor membranes, such as Group III-V membranes (e.g., InGaAs), Ge membranes, and dichalcogenide membranes which undergo a strain-induced direct bandgap transition with strain. The piezoelectric device could also be used in radiofrequency nanoelectromechanical (RF-NEMS) devices, where piezoelectric activity is used for active antenna applications.

Additional device applications are enabled by forming one or more apertures in the piezoelectric substrate and bonding the semiconductor membrane to the surface of the piezoelectric substrate around the perimeter of the one or more apertures, such that a portion of the membrane is suspended over the one or more apertures. For example, a semiconductor membrane bonded to a piezoelectric substrate and suspended over an aperture in the piezoelectric substrate can be acoustically coupled to the substrate, such that surface wave induced in the piezoelectric substrate by the application of an electric signal to the substrate are conducted to the semiconductor membrane. Devices of this type have applications as eardrum transducers, as described in U.S. patent application publication number 2020/0092666.

In another application, one or more through-holes (illustrated in FIG. 2, left panels) are defined in the semiconductor membrane, such that the semiconductor membrane—piezoelectric substrate structure can be used as a micro- or nano-valve. By applying an electric signal to the piezoelectric substrate, the substrate aperture can be reversible expanded and contracted, resulting in the opening and closing of the one or more holes in the semiconductor membrane.

Another application for a structure in which the piezoelectric substrate defines an aperture and the semiconductor membrane includes one or more through-holes is in nanopore DNA sequencing. In nanopore DNA sequencing the membrane defines one or more through-holes sized to allow a single DNA molecule to pass. As a DNA molecule traverses the through-hole, different bases generate different electric current densities across the hole. In this manner, the through-hole acts as an antenna. A second antenna can be positioned to electrically couple to the nanopore antenna. The sequence of the DNA can be determined by measuring the resulting current fluctuations. The magnitude of electric current density across a through-hole depends on the diameter of the hole and the composition of the DNA that occupies the hole. Using the semiconductor membrane-piezoelectric substrate structures described herein, the through-hole diameter can be modulated by applying an electric signal to the piezoelectric substrate that induces a strain in the membrane. More details regarding the operation and microelectronic components and circuitry of nanopore DNA sequencers can be found in U.S. patent application publication number 2016/0025655.

Example

This example illustrates the fabrication of composite semiconductor membrane-piezoelectric substrate structures that include a single-crystalline semiconductor (silicon) nanomembrane bonded to a machined and polished bulk PZT substrate having a circular opening defined therein. Although these are the specific materials used in this example, the process described here can be used with other semiconductors and piezoelectric materials.

To prepare the substrates, the membrane-bonding surfaces of bulk PZT wafers were polished to an RMS roughness of approximately 40 nm. The polishing was achieved by mounting the PZT wafer to a lapping plate with Crystal Bond, and polishing with varying sized suspended alumina media (down to 0.05 micron) on a Logitec PM5 manual polisher. Holes from 100-200 microns were mechanically drilled using 100-200 micron drill bits.

The silicon nanomembranes were obtained by releasing the device layers from silicon-on-insulator (SOI) substrates. The process generally started with 220 nm device layer thickness SOI that was thinned to the desired thickness (74 nm, 112 nm, and 220 nm) using cycles of wet thermal oxidation in a Tystar oxidation furnace and sacrificial oxide stripping in hydrofluoric acid (HF). The SOI substrate was patterned to define the size of the membrane with standard photolithography, using 1813 (Shipley) photoresist (PR). The photoresist was applied by spin coating according to the manufacturer's instructions. Silicon membranes having thickness of 74 nm, 112 nm, and 220 nm were released from SOI substrates by selectively etching the buried oxide layer (which is an intermediate layer between the membrane and handle wafer) in 49% HF. For the membranes thinner than 120 nm, the PR layer was left intact on the surface of the device layer prior to its release. This PR layer serves as a buoyancy aid for thin membranes and enables easier handling. After membrane release in HF and a subsequent distilled deionized (DI) water rinse, the PR coating was removed using N-N dimethylacetamide, which minimized damage to the membranes during the subsequent water transfer to the polished PZT substrates. The water transfer method employed a wire loop, which was used to "fish" the membranes out of the DI water by forming a thin film of water containing the membrane within the loop. This water film-membrane was then transferred to the PZT substrate by contacting the loop to the substrate, causing the water containing the membrane to transfer to the substrate. Generally, the substrate/membrane was heated on a hotplate at up to 120° C. for 30 min to evaporate the water; although this step is not required, it shortens the time for water evaporation.

The procedure described above produced samples having relatively flat silicon membranes over the circular holes (apertures) in the PZT substrates and good bonding between the silicon nanomembranes and the PZT around the perimeters of the holes. Notably, the method of bonding the silicon membranes to the PZT does not require deleterious high-temperature processing and intermediate layers. Therefore, the integrity of the membranes and any devices that have been patterned on the membranes can be maintained, and the need to re-pole the PZT can be circumvented, as no thermal treatment is required.

Figure 2:
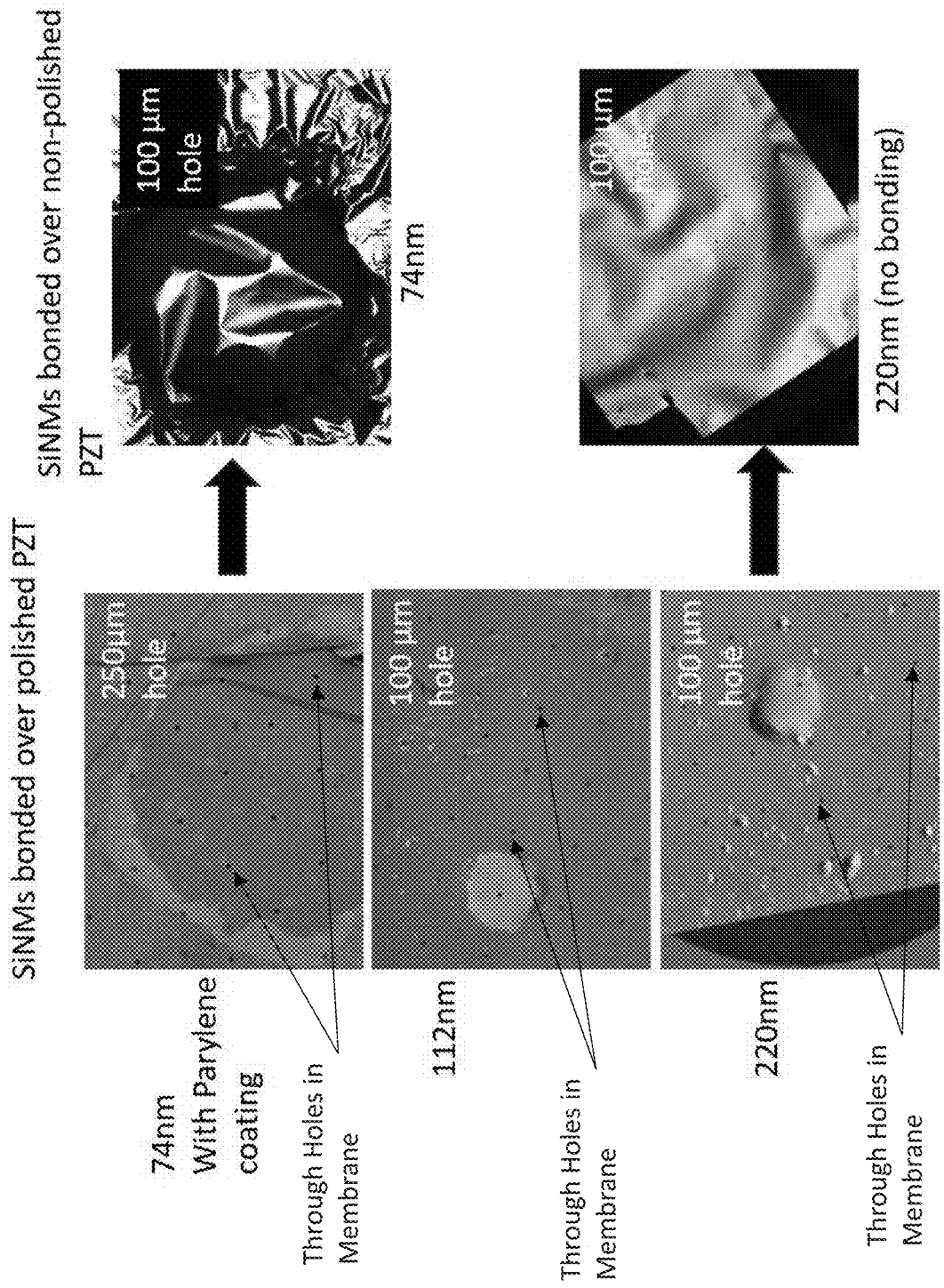
FIG. 2 Optical micrographs of silicon nanomembranes (SiNMs) of varying thicknesses bonded over holes in lead zirconium titanate (PZT) substrates. The PZT in the left panels was polished to 43 nm Root Mean Square (RMS) surface roughness. The PZT in the right panels was unaltered from the manufacturer and had an RMS surface roughness>500 nm.

FIG. 2 shows that polishing the PZT substrates resulted in significantly flatter membranes bonded around the hole, resulting in flatter suspended membranes over the hole and significantly better bonding of the two materials. The rings visible in some of the images are from gold electrodes patterned on the PZT prior to transfer. The images in the right panel (non-polished PZT) demonstrate rippling in the bonded membrane (74 nm) and no bonding at all (220 nm). FIG. 2 further demonstrates that this general method works for membranes of various thickness.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A piezoelectric transducer comprising:
    a piezoelectric substrate consisting of a piezoelectric material and having a surface with a surface roughness of no greater than 100 nm RMS;
    a semiconductor membrane having a thickness of 5 μm or less bonded directly to the piezoelectric material at the surface, such that no other material is applied or inserted between the piezoelectric material and the semiconductor membrane; and
    a set of electrodes in electrical communication with the piezoelectric substrate and configured to apply an electric signal to the piezoelectric substrate.

2. The transducer of claim 1, wherein the surface has a surface roughness of no greater than 50 nm RMS.

3. The transducer of claim 1, wherein the semiconductor membrane has a thickness of no greater than 500 nm.

4. The transducer of claim 3, wherein the semiconductor membrane has a thickness of no greater than 100 nm.

5. The transducer of claim 1, wherein the semiconductor membrane comprises a Group IV semiconductor.

6. The transducer of claim 5, wherein the semiconductor membrane is a silicon membrane.

7. The transducer of claim 1, wherein the piezoelectric material is doped or undoped lead zirconium titanate.

8. The transducer of claim 7, wherein the semiconductor membrane is a silicon membrane.

9. The transducer of claim 1 further comprising an external voltage source configured to apply a voltage across the piezoelectric substrate.

10. The transducer of claim 1 further comprising one or more electronic devices integrated into the semiconductor membrane.

11. The transducer of claim 1, wherein an aperture is defined in the piezoelectric substrate and a portion of the semiconductor membrane is suspended over the aperture.

12. The transducer of claim 11, wherein one or more holes are defined in the portion of the semiconductor membrane that is suspended over the aperture.

13. The transducer of claim 1, wherein the piezoelectric material is lead zirconium titanate lithium niobate, lead magnesium niobate-lead titanate (PMN-PT), lead zinc niobate lead titanate (PZN-PT), $LiNbO_3$, gallium phosphate, quartz, or tourmaline.

* * * * *